(12) United States Patent
Mathew

(10) Patent No.: US 8,571,280 B2
(45) Date of Patent: Oct. 29, 2013

(54) TRANSMISSION OF MEDICAL IMAGE DATA

(75) Inventor: Manoj Mathew, Tustin, CA (US)

(73) Assignee: Canon Kabushiki Kaisha, Tokyo (JP)

( * ) Notice: Subject to any disclaimer, the term of this patent is extended or adjusted under 35 U.S.C. 154(b) by 482 days.

(21) Appl. No.: 12/710,262

(22) Filed: Feb. 22, 2010

(65) Prior Publication Data
US 2011/0206249 A1  Aug. 25, 2011

(51) Int. Cl.
*G06K 9/00* (2006.01)
*G06K 9/34* (2006.01)

(52) U.S. Cl.
USPC ........................................................ 382/128

(58) Field of Classification Search
USPC ......... 382/100, 128–132, 190, 201, 203, 266, 382/294; 600/373, 374, 407, 408, 453; 707/200; 713/176; 358/3.28
See application file for complete search history.

(56) References Cited

U.S. PATENT DOCUMENTS

| | | | |
|---|---|---|---|
| 4,800,379 A | 1/1989 | Yeomans | |
| 5,125,043 A | 6/1992 | Karlsson | |
| 5,416,602 A | 5/1995 | Inga et al. | |
| 6,058,322 A * | 5/2000 | Nishikawa et al. | 600/408 |
| 6,236,766 B1 | 5/2001 | Zavaljevski et al. | |
| 6,418,237 B1 * | 7/2002 | Takeo | 382/128 |
| 6,621,918 B1 | 9/2003 | Hu et al. | |
| 6,766,044 B1 | 7/2004 | Tsujii | |
| 6,792,153 B1 | 9/2004 | Tsujii | |
| 7,031,506 B2 | 4/2006 | Tsujii et al. | |
| 7,231,522 B2 * | 6/2007 | Murakami et al. | 713/176 |
| 7,376,279 B2 | 5/2008 | Dekel et al. | |
| 7,415,169 B2 * | 8/2008 | Florent et al. | 382/294 |
| 7,420,593 B2 | 9/2008 | Tunoda | |
| 7,457,431 B2 * | 11/2008 | Shi et al. | 382/100 |
| 7,489,825 B2 | 2/2009 | Sirohey et al. | |
| 7,492,821 B2 | 2/2009 | Berman et al. | |
| 7,529,427 B2 | 5/2009 | Schweng | |
| 7,602,950 B2 | 10/2009 | Goldstein et al. | |
| 8,059,815 B2 * | 11/2011 | Lofgren et al. | 380/201 |
| 2002/0021758 A1 | 2/2002 | Chui | |
| 2002/0051583 A1 | 5/2002 | Brown et al. | |
| 2002/0057850 A1 | 5/2002 | Sirohey et al. | |
| 2002/0089502 A1 | 7/2002 | Matchen | |
| 2002/0105531 A1 | 8/2002 | Niemi | |
| 2002/0191867 A1 | 12/2002 | Le et al. | |
| 2004/0139121 A1 * | 7/2004 | Nagaraj et al. | 707/200 |
| 2005/0002547 A1 | 1/2005 | Torre-Bueno | |
| 2005/0101856 A1 | 5/2005 | Judd et al. | |
| 2006/0036626 A1 | 2/2006 | Judd et al. | |
| 2008/0120372 A1 | 5/2008 | Kariathungal et al. | |
| 2009/0279764 A1 | 11/2009 | Kaji et al. | |
| 2011/0206249 A1 * | 8/2011 | Mathew | 382/128 |

* cited by examiner

*Primary Examiner* — Amir Alavi
(74) *Attorney, Agent, or Firm* — Fitzpatrick, Cella, Harper & Scinto

(57) ABSTRACT

Transmission of a medical image such as a DICOM-formatted image which is formatted into a plurality of data sets including a data set for the image data and a data set for embedded information which identifies the nature of the medical image. A region of interest in the medical image is identified automatically by using the embedded information. Image data for the region of interest is transmitted, and image data for a region other than the region of interest is transmitted. Transmission of the image data for the entirety of the region of interest is completed before transmission of the image data for the entirety of the region other than the region of interest.

30 Claims, 9 Drawing Sheets

CPT = 73060 = "Humerus"
Modality = XA = "X-RAY"
Imaging Position = AP = "Anterio-Posterior"

Estimate Region of Interest

TRANSMISSION OF MEDICAL IMAGE DATA

FIELD

The present disclosure relates to transmission of medical image data such as DICOM-formatted medical image data, and more particularly relates to transmission of medical image data to a remote location or device.

BACKGROUND

In medical imaging, it is common to transmit medical image data from a first station to a second station which may be located remotely from the first station. For example, a technician may transmit medical image data from a digital radiology device to a doctor or analyst elsewhere in the hospital, or outside the hospital entirely. By transmitting the medical image data remotely, there is ordinarily no need for the doctor or analyst to be present at each machine where medical image data is stored.

In one example, an entire medical image is transmitted to the doctor or analyst directly from a CAT scan, or shortly after the time of scanning. In this way, the doctor or analyst can make decisions based on the entirety of the image data obtained for a particular patient.

SUMMARY

One difficulty in transmitting the entire medical image is that such images tend to be relatively large, owing to enhanced resolution and pixel bit depth. Accordingly, transmission of the entire medical image consumes significant bandwidth and network resources and can lead to significant transmission delays, especially when transmission is to a remote device such as a PDA or other mobile device. These transmission delays increase the time needed for the doctor or analyst to return a diagnosis or decision.

The foregoing is addressed by automatically identifying and transmitting a region of interest in the medical image, prior to transmission of the rest of the medical image.

In example embodiments described herein, the region of interest is identified automatically, based on embedded information which identifies the nature of the medical image, and which is formatted as part of the image itself.

Thus, in an example embodiment described herein, for a medical image formatted into a plurality of data sets including a data set for the image data and a data set for embedded information which identifies the nature of the medical image, a region of interest in the medical image is identified automatically by using the embedded information. Image data for the region of interest is transmitted, followed by transmission of image data for a region other than the region of interest. Transmission of the image data for the entirety of the region of interest is completed before transmission of the image data for the entirety of the region other than the region of interest.

By automatically identifying and transmitting a region of interest in the medical image prior to transmission of the rest of the medical image, it is ordinarily possible to improve the speed of analysis and diagnosis, even if the doctor or analyst is using a remote device. Specifically, since a smaller region of interest is transferred first, the doctor or analyst can analyze relevant data sooner, ordinarily avoiding the need to wait for the entirety of the image to be transmitted across the network.

In one example embodiment, the DICOM medical image format satisfies the requirements of a medical image formatted into a plurality of data sets including a data set for the image data and a data set for embedded information which identifies the nature of the medical image. For example, the DICOM format may include embedded information such as a current procedural terminology (CPT) code for the medical image, and the region of interest can be identified automatically based at least in part on the CPT code.

This brief summary has been provided so that the nature of this disclosure may be understood quickly. A more complete understanding can be obtained by reference to the following detailed description and to the attached drawings.

DETAILED DESCRIPTION

Figure 1:
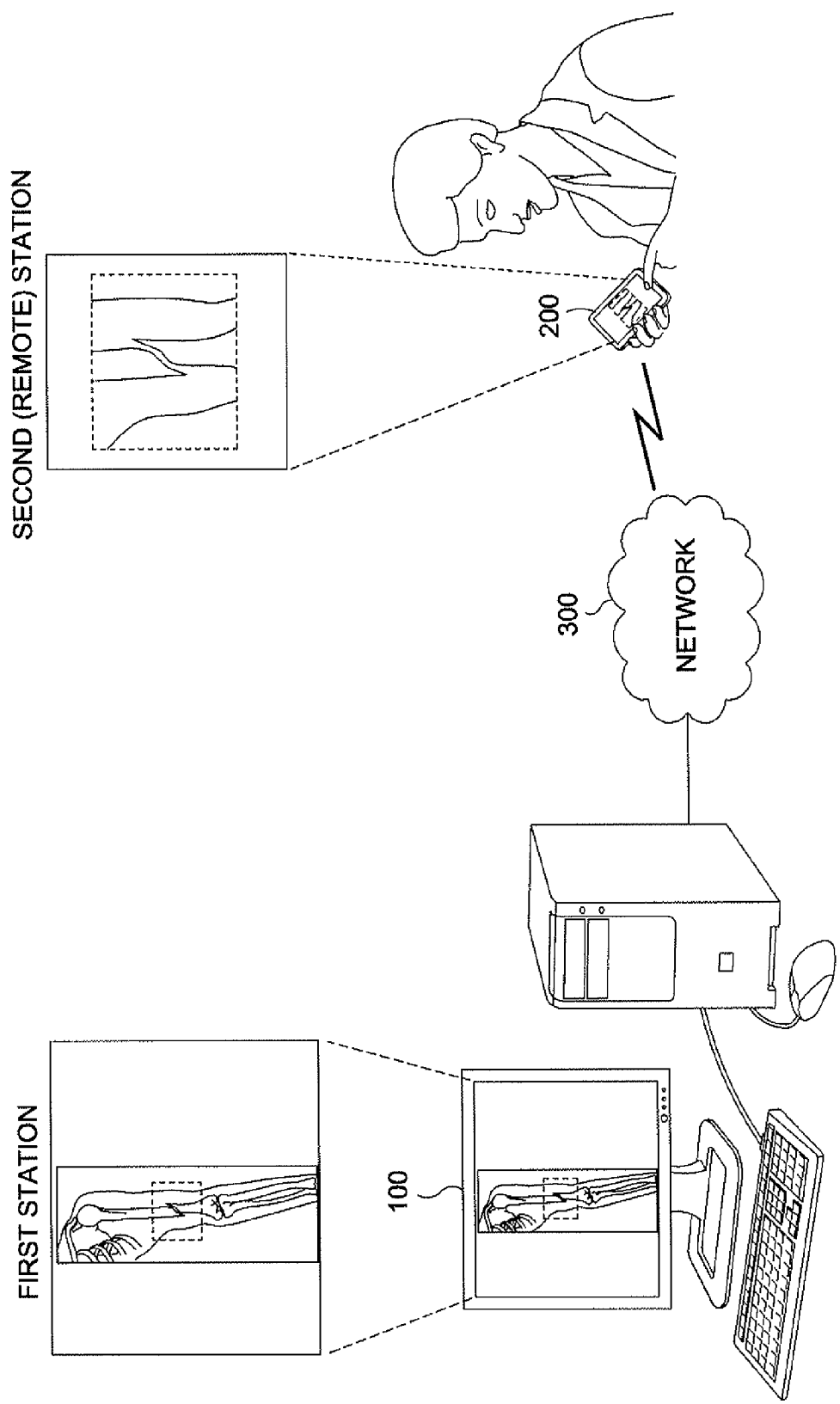
FIG. 1 illustrates an example embodiment of an environment in which aspects of the present disclosure may be practiced.

FIG. 1 illustrates an example environment in which aspects of the present disclosure may be practiced. Computer 100 is located at a first station, and generally comprises a programmable general purpose personal computer having an operating system, such as Microsoft® Windows® or Apple® Mac OS® or LINUX, and which is programmed as described below so as to perform particular functions and, in effect, become a special purpose computer when performing these functions.

As shown in FIG. 1, computer 100 displays a medical image on a display screen. Computer 100 is connected to client device 200 via network 300. Computer 100 and client device 200 communicate via network 300 to transmit data and commands.

While FIG. 1 depicts a computer, computing equipment for practicing aspects of the present disclosure can be implemented in a variety of embodiments. For example, in a medical image processing environment, the computing equipment might be a CT scanner, an X-ray machine or an MRI machine, among many others. Other embodiments are possible according to the application and environment.

Computer 100 also includes computer-readable memory media, such as fixed disk 45 (shown in FIG. 2), which is constructed to store computer-readable information, such as computer-executable process steps or a computer-executable program for causing a computer to perform a method for transmitting a medical image, as described more fully below.

Client device 200 displays part of the medical image from computer 100, and accepts inputs from a user such as a doctor or x-ray technician. Physically, client device 200 can be embodied as a number of devices, including, for example, a personal digital assistant (PDA) as shown in FIG. 1, a computer, a cellular telephone, or a portable media player, among many other embodiments.

Network 300 transmits data between computer 100 and client device 200. The implementation, scale and hardware of network 300 may vary according to different embodiments. Thus, for example, network 300 could be the Internet, a Local Area Network (LAN), Wide Area Network (WAN), Metropolitan Area Network (MAN), or Personal Area Network (PAN), among others. Network 300 can be wired or wireless, and can be implemented, for example, as an Optical fiber, Ethernet, or Wireless LAN network. In addition, the network topology of network 300 may vary.

Figure 2:
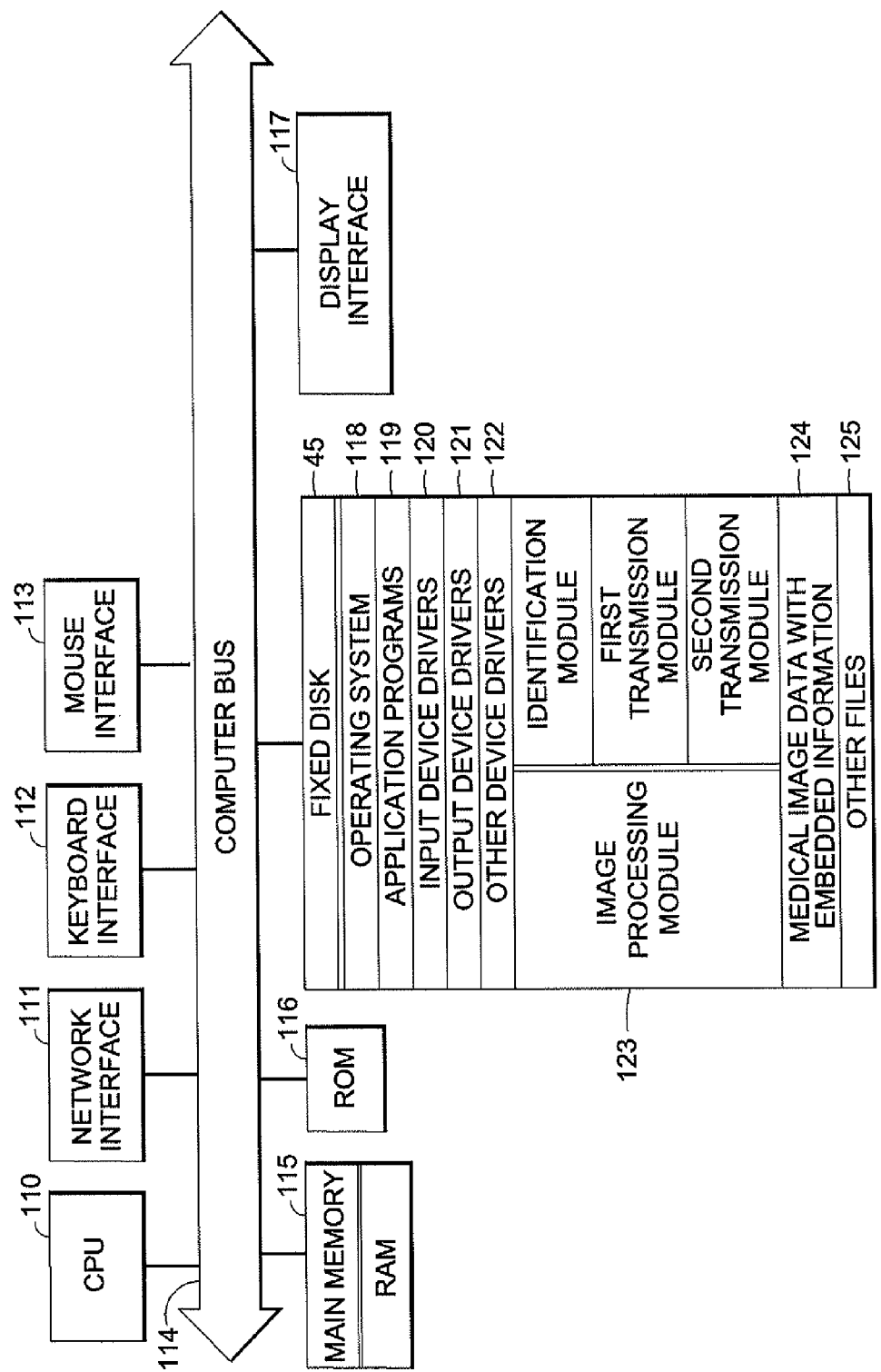
FIG. 2 is a detailed block diagram depicting the internal architecture of the computer shown in FIG. 1.

FIG. 2 is a detailed block diagram depicting the internal architecture of the computer 100 shown in FIG. 1. As shown in FIG. 2, computer 100 includes central processing unit (CPU) 110 which interfaces with computer bus 114. Also interfacing with computer bus 114 are fixed disk 45 (e.g., a hard disk or other nonvolatile storage medium), network interface 111, keyboard interface 112, mouse interface 113, random access memory (RAM) 115 for use as a main runtime transient memory, read only memory (ROM) 116, and display interface 117 for a display screen or other output.

RAM 115 interfaces with computer bus 114 so as to provide information stored in RAM 115 to CPU 110 during execution of the instructions in software programs, such as an operating system, application programs, image processing modules, and device drivers. More specifically, CPU 110 first loads computer-executable process steps from fixed disk 45, or another storage device into a region of RAM 115, CPU 110 can then execute the stored process steps from RAM 115 in order to execute the loaded computer-executable process steps. Data, such as medical image data with embedded DICOM annotation data, or other information, can be stored in RAM 115 so that the data can be accessed by CPU 110 during the execution of the computer-executable software programs, to the extent that such software programs have a need to access and/or modify the data.

As also shown in FIG. 2, fixed disk 45 contains computer-executable process steps for operating system 118, and application programs 119, such as graphic image management programs. Fixed disk 45 also contains computer-executable process steps for device drivers for software interface to devices, such as input device drivers 120, output device drivers 121, and other device drivers 122. Medical image data with embedded information 124 is available for processing. In addition, other files 125 are available for output to output devices and for manipulation by application programs.

Figure 4:
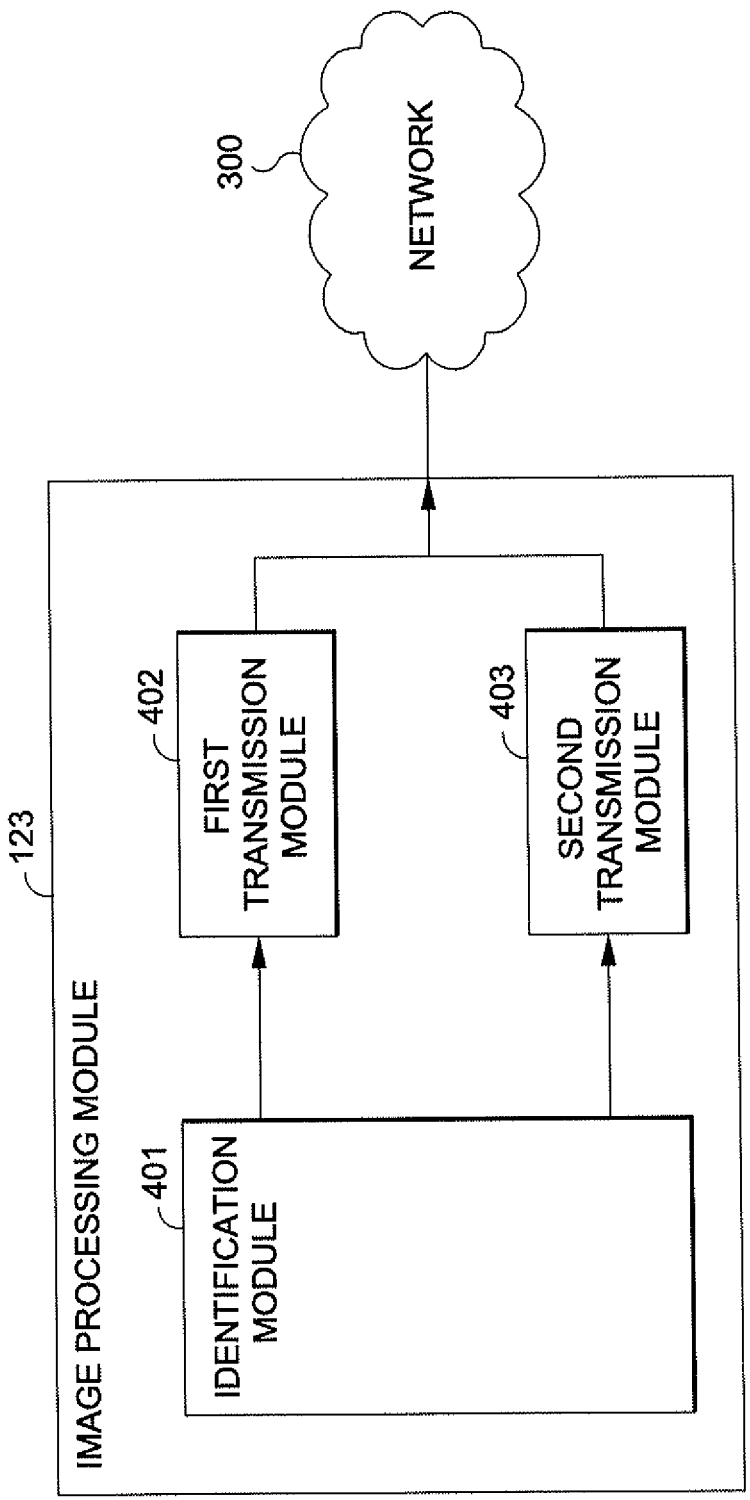
FIG. 4 illustrates an example of an image processing module.

Image processing module 123 comprises computer-executable process steps for transmitting a medical image. Image processing module 123 generally comprises an identification module, a first transmission module, and a second transmission module, as shown in FIG. 4.

More specifically, image processing module 123 is configured to identify a region of interest in a medical image, and to subsequently transmit the region of interest and a region other than the region of interest to another device, such as client device 200. This process will be described in more detail below.

The computer-executable process steps for image processing module 123 may be configured as part of operating system 118, as part of an output device driver, such as an image processing driver, or as a stand-alone application program. Image processing module 123 may also be configured as a plug-in or dynamic link library (DLL) to the operating system, device driver or application program. In one example embodiment described herein, image processing module 123 is incorporated directly into the operating system for computer 100. It can be appreciated that the present disclosure is not limited to these embodiments and that the disclosed modules may be used in other environments.

Figure 3:
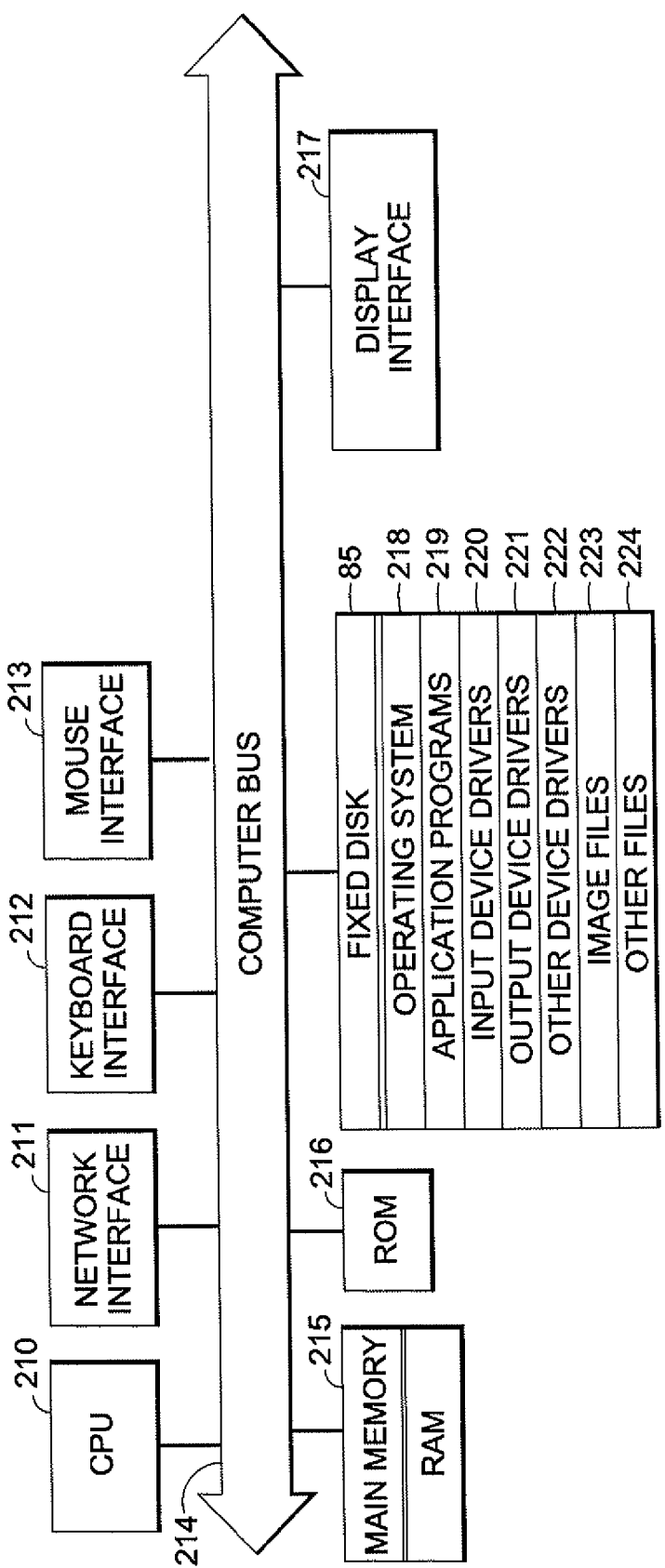
FIG. 3 is a detailed block diagram depicting the internal architecture of the client device shown in FIG. 1.

FIG. 3 is an architecture diagram of an example embodiment of a client device, such as the PDA shown in FIG. 1. As shown in FIG. 3, client device 200 includes central processing unit (CPU) 210 which interfaces with computer bus 214. Also interfacing with computer bus 214 are fixed disk 85 (e.g., a hard disk or other nonvolatile storage medium), network interface 211, keyboard interface 212, mouse interface 213, random access memory (RAM) 215 for use as a main runtime transient memory, read only memory (ROM) 216, and display interface 217 for a display screen or other output.

RAM 215 interfaces with computer bus 214 so as to provide information stored in RAM 215 to CPU 210 during execution of the instructions in software programs, such as an operating system, application programs, image processing modules, and device drivers. More specifically, CPU 210 first loads computer-executable process steps from fixed disk 85, or another storage device into a region of RAM 215. CPU 210 can then execute the stored process steps from RAM 215 in order to execute the loaded computer-executable process steps. Data, such as image data with embedded DICOM annotation data, or other information, can be stored in RAM 215 so that the data can be accessed by CPU 210 during the execution of the computer-executable software programs, to the extent that such software programs have a need to access and/or modify the data.

As also shown in FIG. 3, fixed disk 85 contains computer-executable process steps for operating system 218, and application programs 219, such as word processing programs or graphic image management programs. Fixed disk 85 also contains computer-executable process steps for device drivers for software interface to devices, such as input device drivers 220, output device drivers 221, and other device drivers 222. Image files 223, including medical image files, are available for view by the user. In addition, image files 223 and other files 224 are available for output and for manipulation by application programs.

FIG. 4 illustrates one example of an image processing module for transmitting medical image data.

In particular, FIG. 4 illustrates an example of image processing module 123 in which the sub-modules of image processing module 123 are included in fixed disk 45. Specifically, FIG. 4 illustrates an example of an image processing module 123 for transmitting a medical image which is formatted into a plurality of data sets including a data set for the image data and a data set for embedded information which identifies the nature of the medical image. Image processing module 123 may comprise a number of sub-modules, as described more fully below. Each of the sub-modules are computer-executable software code or process steps executable by a processor, such as CPU 110, and are stored on a computer-readable storage medium, such as fixed disk 45 or RAM 115. More or less modules may be used, and other architectures are possible.

As shown in FIG. 4, image processing module 123 includes identification module 401 for identifying a region of interest in the medical image. The region of interest is identified automatically by using information embedded in the medical image. Image processing module 123 also includes a first transmission module 402 for transmitting image data for the region of interest, and a second transmission module 403 for transmitting image data for a region other than the region of interest.

Figure 5:
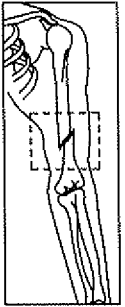
FIG. 5 is view for explaining medical image data formatted with embedded information.

FIG. 5 is view for explaining medical image data formatted with embedded information, and in particular is a simplified view of a format of a DICOM file for medical image data. As shown in FIG. 5, the DICOM file includes a set of attributes with particular values, including a pixel data attribute containing the medical image. The DICOM file also includes attributes for a patient ID, an imaging modality code identifying the imaging modality (e.g., X-ray), a CPT code identifying the nature of the image, an imaging position code for indicating the position from which the image was taken, and a code indicating the number of frames in the DICOM file. For purposes of conciseness, examples of all possible DICOM attributes and values are omitted. However, additional information and examples regarding DICOM can be found at, for example, DICOM Standard 3.1 to PS. 3.18 (NEMA Standard PS3, 2009), the contents of which are incorporated by reference herein.

A process for transmitting a medical image formatted into a plurality of data sets, including a data set for the image data and a data set for embedded information which identifies the nature of the medical image, will now be described with respect to FIG. 6.

Figure 6:
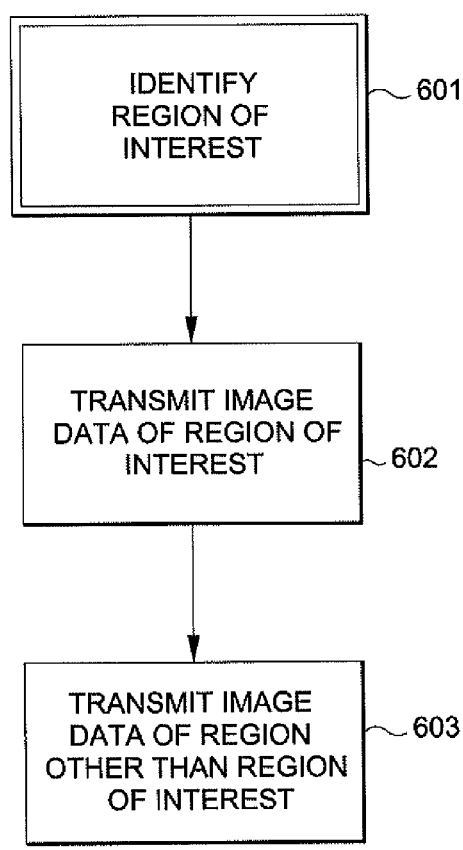
FIG. 6 is a flowchart illustrating an example process for transmitting a medical image.

Briefly, as shown in FIG. 6, for a medical image formatted into a plurality of data sets including a data set for the image data and a data set for embedded information which identifies the nature of the medical image, a region of interest in the medical image is identified automatically by using the embedded information. Image data for the region of interest is transmitted, followed by transmission of image data for a region other than the region of interest. Transmission of the image data for the entirety of the region of interest is completed before transmission of the image data for the entirety of the region other than the region of interest.

In step 601, a region of interest is identified automatically by computer 100. The region of interest is identified automatically using the embedded information.

Specifically, the medical image data is formatted into a plurality of data sets including a data set for the image data and a data set for embedded information which identifies the nature of the medical image. Thus, for example, a chest x-Ray image file actually contains embedded information regarding the imaging modality, the imaging position code, the patient, and so on.

In one example, the embedded information can include information identifying an imaging modality for the medical image, and the region of interest can identified automatically based at least in part on the imaging modality. In another example, the embedded information can include information identifying an imaged anatomical feature in the medical image, and the region of interest can identified automatically based at least in part on the imaged anatomical feature. In still another example, the embedded information can include a current procedural terminology (CPT) code for the medical image, and the region of interest can identified automatically based at least in part on the CPT code. In yet another example, the embedded information can include information identifying a radiographic position and a direction of imaging for the medical image, and the region of interest can identified automatically based at least in part on the radiographic position and the direction of imaging.

The DICOM medical image format satisfies the requirements of a medical image formatted into a plurality of data sets including a data set for the image data and a data set for embedded information which identifies the nature of the medical image. For example, the DICOM format may include embedded information such as a current procedural terminology (CPT) code for the medical image, and the region of interest can be identified automatically based at least in part on the CPT code.

Computer 100 uses the embedded information to estimate the region of interest. For example, if the embedded DICOM codes indicate that the medical image data is an x-ray of an ankle taken from above, then it can be estimated that the region of interest will be in the center of the entire medical image, according to x-ray procedures used for that type of image. Of course, the estimated region of interest may differ according to the various types of medical images. Correspondences between different sets of DICOM codes and respective regions of interest can be stored in a look-up table or other format, and can be stored, for example, on fixed disk 45 of computer 100.

The region of interest may comprise only a small part of the entire medical image. For example, the region of interest may comprise only 20% of the total medical image. Accordingly, the region of interest can be transmitted more quickly than by transmitting the entirety of the medical image data, and such transmission can ordinarily be accomplished using less bandwidth and processing resources. Additionally, the extra available bandwidth and resources may allow transmission of the region of interest in a high-resolution format, which provides the doctor or user at the client device with a better picture for examination and/or diagnosis.

In step 602, the identified region of interest is transmitted from computer 100 to client device 200 via network 300.

During the transmission, the region of interest may be scaled from the host device to fit on the client device. For example, different client devices such as PDAs may have different screens, and the region of interest must therefore be scaled to fit the client device appropriately. In that regard, a number of coordinates may be calculated in order to accommodate such scaling, as shown below.

$X_{roi}$: Horizontal X coordinate position of selected region at client
$Y_{roi}$: Vertical Y coordinate position of selected region at client
$W_{roi}$: Width of selected region at client
$H_{roi}$: Height of selected region at client
$X_{mag}$: Horizontal X coordinate position of zoom region at client
$Y_{mag}$: Vertical Y coordinate position of zoom region at client
$W_{mag}$: Width of zoom region at client
$H_{mag}$: Height of zoom region at client
$W_{lr}$: Width of low resolution image at client
$H_{lr}$: Height of low resolution image at client
$X_o$: Horizontal X coordinate position at host
$Y_o$: Vertical Y coordinate position at host
$W_0$: Calculated width of corresponding selection region at host
$H_0$: Calculated height of corresponding selection region at host
$W_{hr}$: Width of high resolution image at host
$H_{hr}$: Height of high resolution image at host
Mag: Magnification Factor For purposes of conciseness, a more detailed explanation of scaling the image to the client device is omitted, although a brief summary of calculations is provided below.

$$R_{lrw} = \frac{X_{roi}}{W_{lr}} \ldots \text{Ratio of } Horz. \text{ ROI position to Width of client}$$

$$R_{lrh} = \frac{Y_{roi}}{H_{lr}} \ldots \text{Ratio of } Vert. \text{ ROI position to Height of client}$$

$$W_o = W_{roi} \times R_{lrw} \qquad X_o = W_{hr} \times R_{lrw}$$
$$H_o = H_{roi} \times R_{lrh} \qquad Y_o = H_{hr} \times R_{lrh}$$
$$W_{mag} = W_{roi} \times Mag \qquad X_{mag} = X_{roi} \times Mag$$
$$H_{mag} = H_{roi} \times Mag \qquad Y_{mag} = Y_{roi} \times Mag$$

The image data for the entirety of the region of interest may be transmitted before transmission of any of the image data for the region other than the region of interest. Thus, transmission may devoted exclusively to the region of interest until transmission of the entirety of the region of interest is complete.

Alternatively, transmission of the image data for the entirety of the region of interest may be completed before transmission of the image data for the entirety of the region other than the region of interest. Thus, while the region other than the region of interest is not delayed completely during transmission of the entirety of the region of interest, transmission is nonetheless controlled so as to ensure that the entirety of the region of interest reaches the client device first.

In yet another example, some but not all of the image data for the region other than the region of interest is transmitted before completion of transmission of the image data for the entirety of the region of interest. The remaining data for the region other than the region of interest is filled in using, for example, wavelet technology.

The data for the region of interest may be compressed prior to transmission to client device 200. In the context of medical image data, it is ordinarily required that any compression method must be lossless. Thus, in one embodiment, the image data for the region of interest is losslessly compressed, and the compressed image data of the region of interest is transmitted. In case of any compression, a very simple means of decompression may be provided to reduce corresponding processing requirements at the client device.

In step 603, the image data for the region other than the region of interest is transmitted to the client device. The image data for the region other than the region of interest may also need to be scaled to fit the client device, as explained above.

The image data for the region other than the region of interest may be reduced in resolution and pixel depth prior to transmission. This reduces the amount of bandwidth and/or processing resources consumed for the region other than the region of interest, allowing the region of interest to be transmitted even more quickly.

As with the image data of the region of interest, the image data of the region other than the region of interest may also be compressed prior to transmission.

In one embodiment of the disclosure, image data of the region of interest is transmitted for multiple frames, for example from a moving image. However, the identification process for identifying the region of interest can be performed generally in the same manner as described above for a single frame. Thus, computer 100 may or may not need to adjust the region of interest for each successive frame, depending on whether the DICOM data of each new frame differs from the previous frame enough to warrant recalibration of the region of interest.

In another embodiment, the doctor or analyst may change the position of the region of interest at the client device. For example, a doctor may receive a region of interest at his or her mobile device, but may wish to scroll upwards to examine a different part of the medical image. In such a case, the system must compensate for these changes and alter the region of interest to correspond to the input. In particular, the new region of interest may deviate from the original region of interest obtained automatically from the DICOM data. Thus, input at client device 200 is transmitted back to computer 100, which re-calculates the region of interest according to the user input and transmits the new region of interest to the client.

An identification of a region of interest according to embedded DICOM medical image data will now be described with respect to FIGS. 7 and 8.

Figure 7:
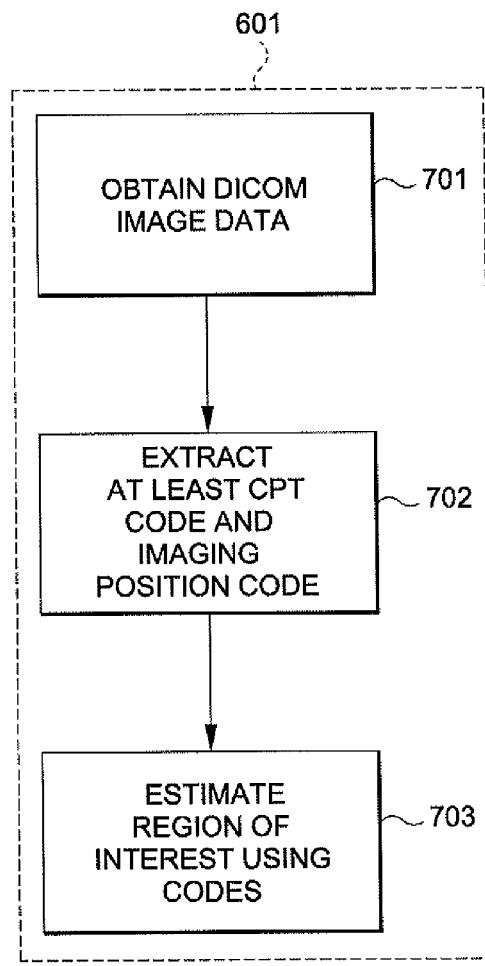
FIG. 7 is a flowchart illustrating an example process for identifying a region of interest.

FIG. 7 is a flowchart illustrating an example process for identifying a region of interest.

In step 701, embedded DICOM data is obtained from the medical image data.

In step 702, computer 100 extracts at least a Current Procedural Terminology (CPT) code and an imaging position code from the DICOM data. The CPT code describes medical, surgical, and diagnostic services, and is designed to communicate uniform information about medical services and procedures among physicians, coders, patients, accreditation organizations, and payers for administrative, financial, and analytical purposes. On the other hand, the imaging position code indicates a radiographic position and a direction of imaging for the medical image, such as Frontal, Medial, Lateral, Axial, Coronal, Palmer, Anterio-posterior (AP) or Postero-anterior (PA).

Ordinarily, computer 100 extracts at least the CPT code and the imaging position code, in order to establish the general type of the image and the angle from which it was taken. Nevertheless, other DICOM data may be extracted and used to further define or refine the region of interest. For example, the DICOM data may also identify the specific anatomical feature imaged, the imaging modality (MRI, ultrasound, panoramic x-ray) used, and so on.

The CPT code or other DICOM data my be changed over time. For example, a doctor may alter the CPT code based on analysis of the region of interest, and this information can be saved in the DICOM data for subsequent processing.

In step 703, the region of interest is estimated using the extracted codes. Specifically, using the CPT code and the imaging position code, it is ordinarily possible to estimate where the region of interest lies, according to operating procedures for that type of image. For example, if the CPT code indicates an x-ray of an ankle and the imaging position code indicates that the image was taken from above, the region of interest will ordinarily lie in the center of the medical image. Of course, the region of interest can vary widely according to the type of image.

As mentioned above, correspondences between different sets of DICOM codes and respective regions of interest can be stored in a look-up table or other format, and can be stored, for example, on fixed disk 45 of computer 100.

Figure 8:
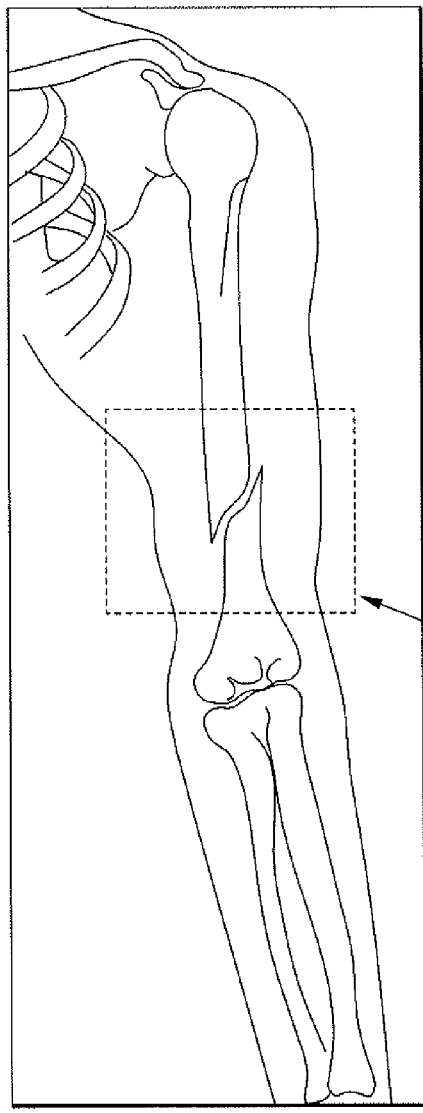
FIG. 8 is a view for explaining the process of identifying a region of interest.

FIG. 8 is a view for explaining selection of a region of interest. More specifically, FIG. 8 depicts the image shown on the display of computer 100, along with some example DICOM codes used to identify the region of interest. As seen in FIG. 8, the codes indicate information about the medical image, which allows for estimation of where an appropriate region of interest should be.

According to one embodiment, the region of interest and region other than the region of interest are transmitted to an image processing server or an image processing cloud, prior to being forwarded to the client device. This process will be described in more detail below with respect to FIGS. 9 and 10.

Figure 9:
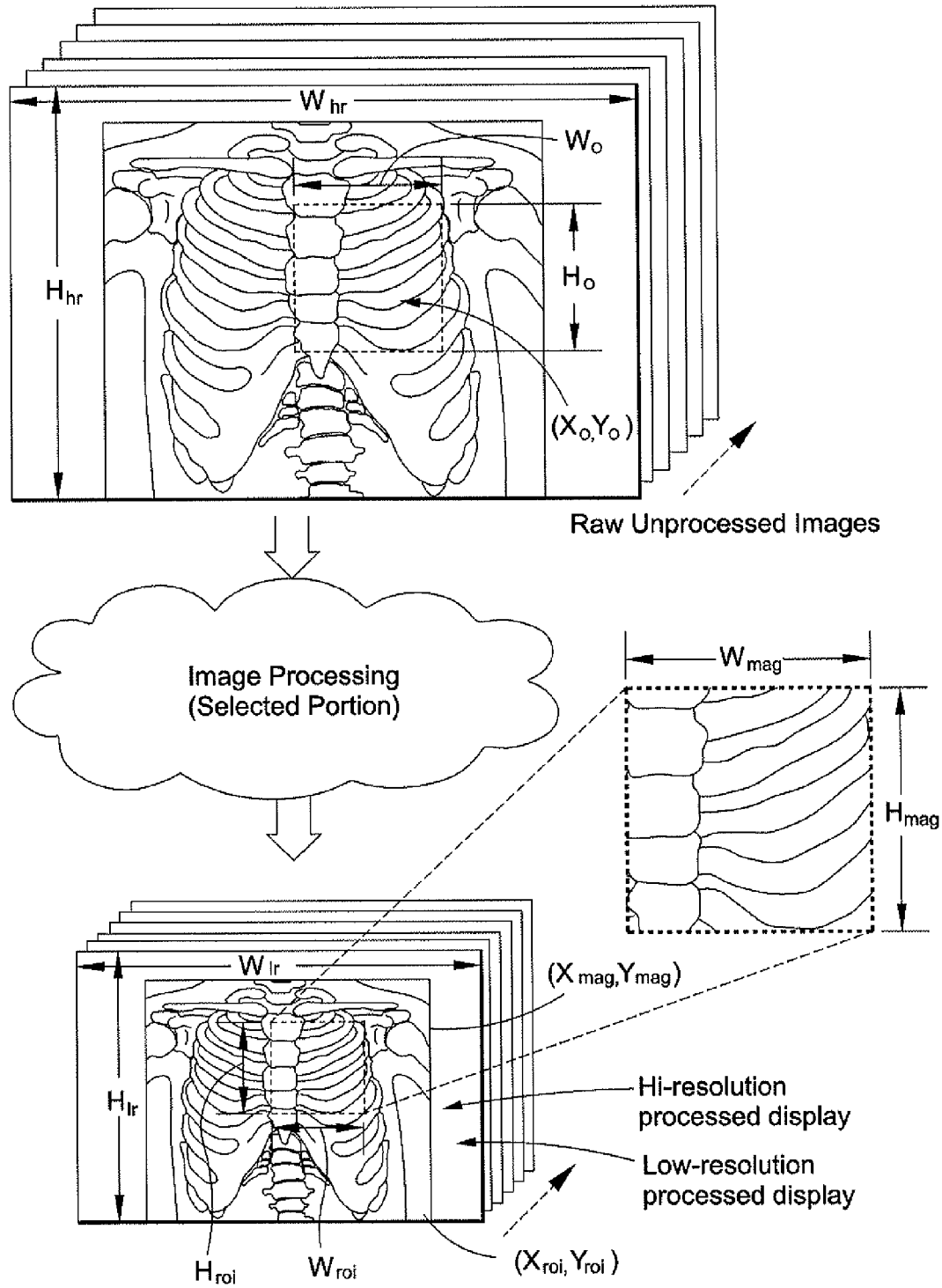
FIG. 9 is a view for explaining transmission of a region of interest to a client device.

As seen in FIG. 9, selected portions of raw unprocessed images at computer 100 are transmitted to a an image processing cloud of computing resources organized to perform image processing. Any number of image processes can be performed, including, for example, image Analysis, Core Image Processing (Contrast Correction, Edge Enhancement, Tone Conversion, Contrast Boost, Artifact Reduction and Offset Calibration. In one example, the image processing cloud may perform high-performance real-time image processing.

The image processing may be performed only on the region of interest to increase processing and transmission speed. Specifically, since the size of region of interest is relatively small, the processing time and bandwidth requirement are reduced.

In another example, both the region of interest and the region other than the region of interest are processed. However, the speed can still be improved by reducing the resolution and/or pixel depth of image data for the region other than the region of interest prior to transmission, so as to reduce processing requirements for the region other than the region of interest. In such a case, the resultant image transmitted to client device 200 may include a high-resolution processed display of the region of interest and a low-resolution processed display of the region other than the region of interest.

Figure 10:
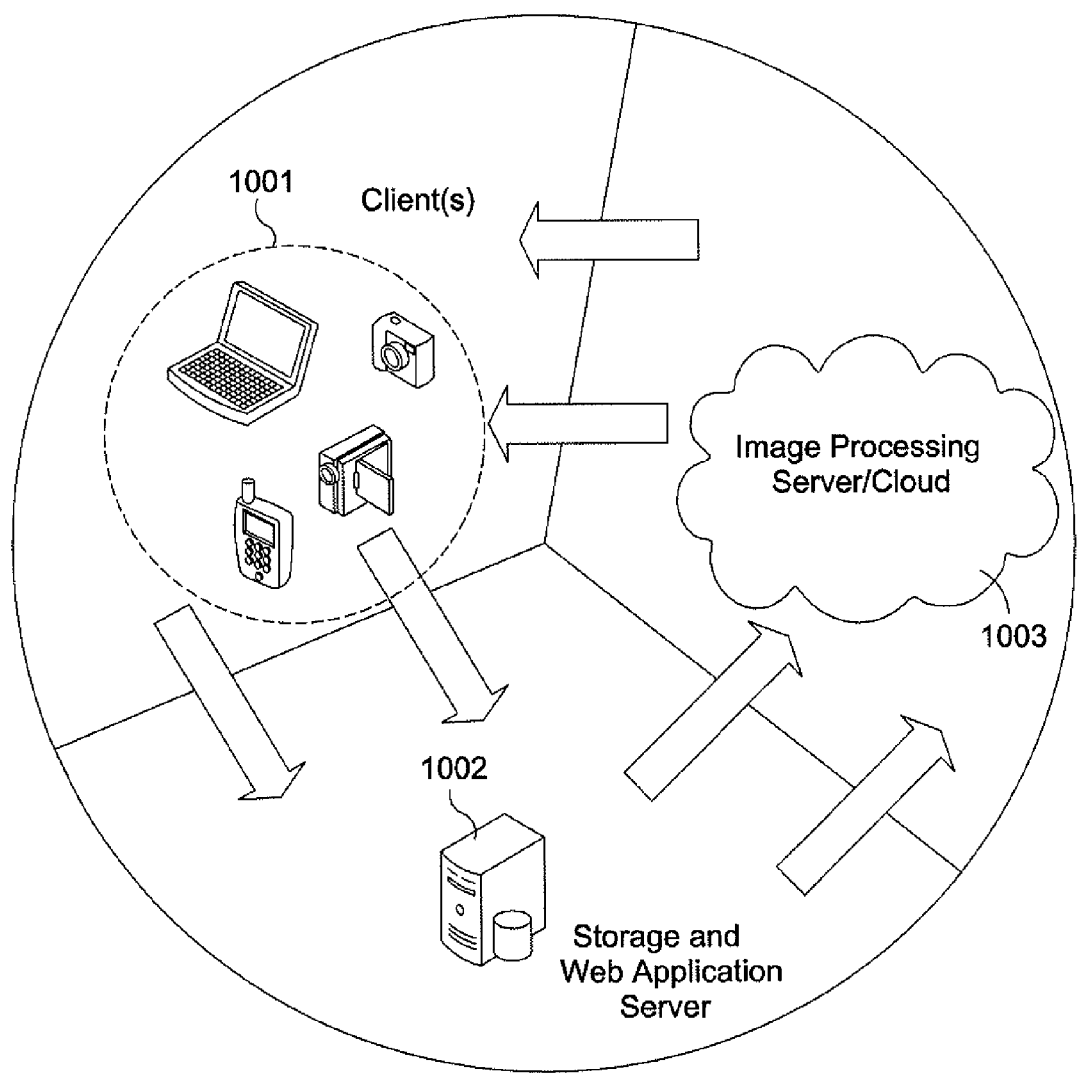
FIG. 10 is a view for explaining an image processing flow between a storage server, an image processing server/cloud, and a client device.

FIG. 10 is a view for explaining an image processing flow between a storage and web application server, an image processing server/cloud, and a client device.

Client device(s) 1001 generally corresponds to client device 200 as described above. As shown in FIG. 10, client device transmits data to storage and web application server 1002. This data may include input movements of the region of interest, as discussed above. Alternatively, the input may request a zoom-in on picture data, request a new image, or various other commands. Additionally, client device 1001 receives processed image data from image processing server/cloud 1003, and displays the data to the client.

In the workflow, storage and web application server 1002 generally performs the functionality of computer 100 described above. As shown in FIG. 10, storage and web application server 1002 receives input from client device 1001. Storage and web application server 1002 performs these commands, for example by adjusting the region of interest to a different section of the medical image. Additionally, storage and web application server 1002 transmits the region of interest and the region other than the region of interest to image processing server/cloud 1003 for processing prior to being forwarded to the client. As described above, the region of interest may be transmitted as a high-resolution image, whereas the region other than the region of interest may be transmitted as a low-resolution image or with less pixel depth.

Image processing server/cloud 1003 can correspond to a single server, or to a cloud of computing resources organized to perform image processing. More specifically, image processing server/cloud 1003 receives image data for the region of interest and region other than the region of interest from storage and web application server 1002, performs the requested processing, and transmits the processed image data to client device 1001. As indicated above, image processing server/cloud 1003 may perform processing on high-resolution data of the region of interest and low-resolution data for the region other than the region of interest.

This disclosure has provided a detailed description with respect to particular representative embodiments. It is understood that the scope of the appended claims is not limited to the above-described embodiments and that various changes and modifications may be made without departing from the scope of the claims.

What is claimed is:

1. A method for transmission of a medical image, wherein the medical image is formatted into a plurality of data sets including a data set for the image data and a data set for embedded information which identifies the nature of the medical image, comprising:
   identifying a region of interest in the medical image, wherein the region of interest is identified automatically by using the embedded information;
   transmitting image data for the region of interest; and
   transmitting image data for a region other than the region of interest,
   wherein transmission of the image data for the entirety of the region of interest is completed before transmission of the image data for the entirety of the region other than the region of interest.

2. The method according to claim 1, wherein the embedded information includes information identifying an imaging modality for the medical image, and wherein the region of interest is identified automatically based at least in part on the imaging modality.

3. The method according to claim 1, wherein the embedded information includes information identifying an imaged anatomical feature in the medical image, and wherein the region of interest is identified automatically based at least in part on the imaged anatomical feature.

4. The method according to claim 1, wherein the embedded information includes a current procedural terminology (CPT) code for the medical image, and wherein the region of interest is identified automatically based at least in part on the CPT code.

5. The method according to claim 1, wherein the embedded information includes information identifying a radiographic position and a direction of imaging for the medical image, and wherein the region of interest is identified automatically based at least in part on the radiographic position and the direction of imaging.

6. The method according to claim 1, further comprising a step of losslessly compressing the image data for the region of interest, wherein the step of transmitting the image data for the region of interest comprises transmitting compressed image data of the region of interest.

7. The method according to claim 6, further comprising a step of losslessly compressing the image data for the region other than the region of interest, wherein the step of transmitting the image data for the region other than the region of interest comprises transmitting compressed image data of the region other than the region of interest.

8. The method according to claim 1, wherein the image data for the entirety of the region of interest is transmitted before transmission of any of the image data for the region other than the region of interest.

9. The method according to claim 1, wherein some but not all of the image data for the region other than the region of interest is transmitted before completion of transmission of the image data for the entirety of the region of interest.

10. The method according to claim 1, wherein image data for multiple frames of the region of interest is transmitted.

11. The method according to claim 1, wherein the image data for the region other than the region of interest is reduced in resolution and pixel depth prior to transmission.

12. The method according to claim 1, wherein the region of interest and region other than the region of interest are transmitted to an image processing server or an image processing cloud for image processing, prior to being transmitted to a destination device.

13. The method according to claim 12, wherein the image processing is performed only on the region of interest.

14. A medical image processing apparatus for transmitting a medical image, wherein the medical image is formatted into a plurality of data sets including a data set for the image data and a data set for embedded information which identifies the nature of the medical image, comprising:
   a computer-readable memory constructed to store computer-executable process steps; and
   a processor constructed to execute the computer-executable process steps stored in the memory;
   wherein the process steps stored in the memory cause the processor to:
   identify a region of interest in the medical image, wherein the region of interest is identified automatically by using the embedded information;
   transmit image data for the region of interest; and
   transmit image data for a region other than the region of interest, wherein transmission of the image data for the entirety of the region of interest is completed before transmission of the image data for the entirety of the region other than the region of interest.

15. The apparatus according to claim 14, wherein the embedded information includes information identifying an imaging modality for the medical image, and wherein the region of interest is identified automatically based at least in part on the imaging modality.

16. The apparatus according to claim 14, wherein the embedded information includes information identifying an imaged anatomical feature in the medical image, and wherein the region of interest is identified automatically based at least in part on the imaged anatomical feature.

17. The apparatus according to claim 14, wherein the embedded information includes a current procedural terminology (CPT) code for the medical image, and wherein the region of interest is identified automatically based at least in part on the CPT code.

18. The apparatus according to claim 14, wherein the embedded information includes information identifying a radiographic position and a direction of imaging for the medical image, and wherein the region of interest is identified automatically based at least in part on the radiographic position and the direction of imaging.

19. The apparatus according to claim 14, further comprising a step of losslessly compressing the image data for the region of interest, wherein the step of transmitting the image data for the region of interest comprises transmitting compressed image data of the region of interest.

20. The apparatus according to claim 19, further comprising a step of losslessly compressing the image data for the region other than the region of interest, wherein the step of transmitting the image data for the region other than the region of interest comprises transmitting compressed image data of the region other than the region of interest.

21. The apparatus according to claim 14, wherein the image data for the entirety of the region of interest is transmitted before transmission of any of the image data for the region other than the region of interest.

22. The apparatus according to claim 14, wherein some but not all of the image data for the region other than the region of interest is transmitted before completion of transmission of the image data for the entirety of the region of interest.

23. The apparatus according to claim 14, wherein image data for multiple frames of the region of interest is transmitted.

24. The apparatus according to claim 14, wherein the image data for the region other than the region of interest is reduced in resolution and pixel depth prior to transmission.

25. The apparatus according to claim 14, wherein the region of interest and region other than the region of interest are transmitted to an image processing server or an image processing cloud for image processing, prior to being transmitted to a destination device.

26. The apparatus according to claim 25, wherein the image processing is performed only on the region of interest.

27. A medical image processing module stored on a non-transitory computer-readable storage medium, for transmitting a medical image, wherein the medical image is formatted into a plurality of data sets including a data set for the image data and a data set for embedded information which identifies the nature of the medical image, comprising:

an identification module for identifying a region of interest in the medical image, wherein the region of interest is identified automatically by using the embedded information;
a first transmission module for transmitting image data for the region of interest; and
a second transmission module for transmitting image data for a region other than the region of interest,
wherein transmission of the image data for the entirety of the region of interest is completed before transmission of the image data for the entirety of the region other than the region of interest.

28. A non-transitory computer-readable storage medium storing computer-executable process steps for causing a computer to perform a method for transmission of a medical image, wherein the medical image is formatted into a plurality of data sets including a data set for the image data and a data set for embedded information which identifies the nature of the medical image, the method comprising:

identifying a region of interest in the medical image, wherein the region of interest is identified automatically by using the embedded information;
transmitting image data for the region of interest; and
transmitting image data for a region other than the region of interest,
wherein transmission of the image data for the entirety of the region of interest is completed before transmission of the image data for the entirety of the region other than the region of interest.

29. A method for transmission of a medical image, wherein the medical image is formatted into a plurality of data sets including a data set for the image data and a data set for embedded information which identifies the nature of the medical image, comprising:

identifying a region of interest in the medical image, wherein the region of interest is identified automatically by using the embedded information;
transmitting image data for the region of interest;
reducing image data for a region other than the region of interest in at least one of resolution and pixel depth;
transmitting the reduced image data;
receiving information indicating a new region of interest; and
transmitting image data for the new region of interest,
wherein transmission of the image data for the entirety of the region of interest is completed before transmission of the image data for the entirety of the region other than the region of interest.

30. A method for transmission of a medical image, wherein the medical image is formatted into a plurality of data sets including a data set for the image data and a data set for embedded information which identifies the nature of the medical image, comprising:

identifying a region of interest in the medical image, wherein the region of interest is identified automatically by using the embedded information;
transmitting image data for the region of interest; and
transmitting image data for a region other than the region of interest,
wherein transmission of the image data for the entirety of the region of interest is ensured to be completed before transmission of the image data for the entirety of the region other than the region of interest.

* * * * *